US008529885B2

(12) United States Patent
Tak et al.

(10) Patent No.: US 8,529,885 B2
(45) Date of Patent: Sep. 10, 2013

(54) AAV VECTORS FOR IN VIVO GENE THERAPY OF RHEUMATOID ARTHRITIS

(75) Inventors: Paul Peter Tak, Leiden (NL); Christian Jorgensen, Lattes (FR)

(73) Assignees: Academisch Medisch Centrum, Amsterdam (NL); Institut National de la Sante et de la Recherche Medicale, Paris (FR)

( * ) Notice: Subject to any disclaimer, the term of this patent is extended or adjusted under 35 U.S.C. 154(b) by 0 days.

(21) Appl. No.: 10/569,851

(22) PCT Filed: Sep. 1, 2004

(86) PCT No.: PCT/NL2004/000607
§ 371 (c)(1),
(2), (4) Date: Nov. 29, 2006

(87) PCT Pub. No.: WO2005/021768
PCT Pub. Date: Mar. 10, 2005

(65) Prior Publication Data
US 2007/0104687 A1    May 10, 2007

(30) Foreign Application Priority Data
Sep. 1, 2003   (NL) .................................. NL03/611

(51) Int. Cl.
*A61K 48/00* (2006.01)
*A61K 31/70* (2006.01)
*C12N 15/63* (2006.01)
*A01K 67/00* (2006.01)

(52) U.S. Cl.
USPC .......................... 424/93.2; 514/44; 435/320.1

(58) Field of Classification Search
USPC ........................................... 424/93.2; 514/44
See application file for complete search history.

(56) References Cited

U.S. PATENT DOCUMENTS

| | | | |
|---|---|---|---|
| 6,515,018 B1 * | 2/2003 | Fuhrman et al. | 514/458 |
| 6,537,540 B1 * | 3/2003 | Burstein et al. | 424/93.2 |
| 7,037,492 B2 * | 5/2006 | Glorioso et al. | 424/93.2 |
| 7,056,502 B2 * | 6/2006 | Hildinger et al. | 424/93.2 |
| 2003/0003583 A1 * | 1/2003 | Hirsch et al. | 435/456 |
| 2003/0013189 A1 * | 1/2003 | Wilson et al. | 435/320.1 |
| 2003/0138772 A1 * | 7/2003 | Gao et al. | 435/5 |
| 2004/0072351 A1 * | 4/2004 | Womer et al. | 435/456 |
| 2004/0191221 A1 * | 9/2004 | Ozawa et al. | 424/93.2 |
| 2005/0019927 A1 * | 1/2005 | Hildinger et al. | 435/456 |
| 2006/0292117 A1 * | 12/2006 | Loiler et al. | 424/93.2 |

FOREIGN PATENT DOCUMENTS

| | | |
|---|---|---|
| JP | 2002-516092 A | 6/2002 |
| WO | WO 99/61601 A2 | 12/1999 |
| WO | WO 00/73481 A1 * | 12/2000 |
| WO | WO 01/11034 A2 | 2/2001 |
| WO | WO 02/101012 A2 | 12/2002 |

OTHER PUBLICATIONS

Zhang et al. Adeno-Associated virus production of soluble tumor necrosis factor receptor neutralizes tumor necrosis factor alpha and reduces arthritis. Human gene therapy 11:2431-2442, 2000.*
Markus Hildinger et al. "Hybrid Vectors Based on Adeno-Associated Virus Serotypes 2 and 5 for Muscle-Directed Gene Transfer". Journal of Virology 75:6199-6203. Jul. 2010.
Adriaansen et al. Ann. Rheum. Dis., 2005.64:1677-84.
Manning, WC et al. (Mar. 1998) Hum. Gene Ther. 9:477-85.
Boyle, MP et al. (Mar. 2003) Hum. Gene Ther. 14:365-73.
Gao, G-P et al. (Sep. 2002) Proc Natl Acad Sci USA 99: 11854-59.
Manno CS et al. (Mar. 2006) Nat Med. 12:342-347.
Jiang H et al. (2006) Blood 108:107-15.
Maguire AM et al. ((May 22, 2008) N. Engl. J Med. 358:2240-48.
Kaplitt MG et al., (Jun. 23, 2007) Lancet 369:2097-2105.
Cottard, V et al., (Mar. 2004) J Clin Immunol. 24:162-9.
Boissier MC et al. (Jun. 2007) Hum Gene Ther. 18:525-35.
Boutin S et al. (Jun. 2010) Hum Gene Ther. 21:704-12.
Bessis, N. et al., "Gene therapy for rheumatoid arthritis." Journal of Gene Medicine 4:581-591 (Nov. 2002).
Davidson, BL et al., "Recombinant adeno-associated virus type 2, 4, and 5 vectors: transduction of variant cell types and regions in the mammalian central nervous system" Proc Nat'l Acad Sci USA 97:3428-3432 (Mar. 2000).
Ghivizzane, SC et al. "Direct gene delivery strategies for the treatment of rheumatoid arthritis", Drug Discovery Today, 6:259-267 (Jan. 2001).
Grimm, D. "Production methods for gene transfer vectors based on adeno-associated virus serotypes." Methods 28146-157 (Oct. 2002).
Hirata R K et al: "Design and packaging of adeno-associated virus gene targeting vectors." J. Virol. 74: 4612-4620 (May 2000).
Pan R-Y et al,,: "Therapy and prevention of arthritis by recombinant adeno-associated virus vector with delivery of interleukin-1 receptor antagonist", Arthritis Rheum. 43: 289-297 (Feb. 2000).
Van De Loo, F.A. et al. : "Gene therapy for rheumatoid arthritis. Lessons from animal models, including studies on interleukin-4, interleukin-10, and interleukin-1 receptor antagonist as potential disease modulators." Rheumatic Diseases Clin N Amer. 28:127-149 (Feb 2002).
Grimm, Dirk "Production Methods for Gene Transfer Vectors Based on Adeno-Associated Virus Serotypes" Methods Oct. 2002, (Stanford, CA, United States), pp. 146-157, vol. 28, No. 2.
Pan, R. Y. et al. "Diseast-Inducible Transgene Expression From a Recombinant Adeno-Associated Virus Vector in a Rat Arthritis Model" Journal of Virology, United States, Apr. 1999, vol. 73, No. 4, pp. 3410-3417.
Ghivizzani, Steven C. et al. "Direct Gene Delivery Strategies for the Treatment of Theumatoid Arthritis" Drug Discovery Today, Jan. 2001, vol. 6, No. 5, pp. 259-267.
Zhang, H. G. et al. "Adeno-Associated Virus Production of Soluble Tumor Necrosis Factor Receptor Neutralized Tumor Necrosis Factor Alpha and Reduces Arthritis" Human Gene Therapy, United States, Nov. 20, 2000, vol. 11, No. 17, pp. 2431-2442.

(Continued)

*Primary Examiner* — Quang Nguyen
(74) *Attorney, Agent, or Firm* — McDonnell Boehnen Hulbert & Berghoff LLP

(57) ABSTRACT

The present invention relates to the field of adeno-associated virus (AAV) based gene therapy, in particular in vivo gene therapy, of rheumatoid arthritis (RA). The invention provides recombinant AAV virions being highly efficient in delivering genes encoding therapeutic proteins to the arthritic joints, and method for using such virions in in vivo gene therapy.

10 Claims, 4 Drawing Sheets

(56) References Cited

OTHER PUBLICATIONS

Bessis, Natacha et al. "Gene Therapy for Rheumatoid Arthritis" The Journal of Gene Medicine, England, Nov. 2002, vol. 4, No. 6, pp. 581-591.

Van De Loo Fons A. J. et al., "Gene Therapy for Rheumatoid Arthritis. Lessons from Animal Models, Including Studies on Interleukin-4, Interluckin-10, and Interleukin-1 Receptor antagonist as potential disease modulators" Rheumatic Diseases Clinics of North America, United States, Feb. 2002, vol. 28, No. 1, pp. 127-149.

Davidson, B. L. et al., "Recombinant Adeno-Associated Virus Type 2,4 and 5 Vectors: Transduction of Variant Cell Types and Regions in the Mammalian Central Nervous System" Proceedings of the National Academy of Sciences of USA, National Academy of Science, Washington, United States, Mar. 28, 2000, vol. 97, No. 7, pp. 3428-3432.

Pan, R. Y. et al. "Therapy and Prevention of Arthritis by Recombinant Adeno-Associated Virus Vector with Delivery of Interleukin-1 Receptor Antagonist" Arthritis and Theumatisn, Feb. 2000, vol. 43, No. 2, pp. 289-297.

Hilding, Markus et al. "Hybrid Vectors Based on Adeno-Associated Virus Serotypes 2 and 5 for Muscle-Directed Gene Transfer", Journal of Virology, Jul. 2001, vol. 75, No. 13, pp. 6099-6203.

Reich, S. J. et al., "Efficient Trans-Splicing in the Retina Expands the Utility of Adeno-Assocated Virus as a Vector for Gene Therapy" Human Gene Therapy, Jan. 1, 2003, vol. 14, No. 1, pp. 37-44.

Hirata R. K. et al., "Design and Packaging of Adeno-Associated Virus Gene Targeting Vectors" Journals of Virology, United States May 2000, vol. 74, No. 10, pp. 4612-4620.

Chernajovsky Y et al. "Gene Therpay for Rheumatoid Arthritis" Theoretical considerations. Drug Aging. Jan. 1998; vol. 12, No. 1, pp. 29-41.

Robbins P.D., "Gene Therapy for Rheumatoid Arthritis" Springer Semin Immunopathol. 1998 vol. 20, Nos. 1-2, pp. 197-209.

Han, Z et al.; "AP-1 and NF-KappaB Regulation in Rheumatoid Arthritis and Murine Collagen-Induced Arthritis. Autoimmunity." 1998; vol. 28, No. 4, pp. 197-208.

Tak P. et al. "Inhibitor of Nuclear Factor KappaB Kinase Beta is a Key Regulator of Synovial Inflamation" Arthritis Theum. Aug. 2001; vol. 44 No. 8; 1897-1907.

Berns et al. "Adeno-Assocated Viruses" An Update. Advances in Virus Research 1987; vol. 32, pp. 243-306.

Clark, K "Highly Purifies Recombinant Adeno-Associated VIrus Vectors are Biologically Active and Free of Detectabel Helper and Wild-Type Viruses" Human Gene Therapy; Apr. 10, 1999; vol. 10, No. 6, pp. 1031-1039.

Flotte, T et al., "An Improved System for Packaging Recombinant Adeno-Associated Virus Vectors Capable of in Vivo Transduction" Gene Therapy Jan. 1995 vol. 2 No. 1 pp. 29-37.

March, C. et al., "Cloning, Sequence and Expression of Two Distince Human Interleukin-1 Complementary DNAs" Nature. Jun. 20-26, 1985, vol. 315 No. 6021 pp. 641-647.

Im SH, et al., "Rat Interleukin-18 Binding Protein: Cloning, Expression, and Characterization" J. Interferon and Cytokine Research, Mar. 2002; vol. 22, No. 3 pp. 321-328.

Grimm D et al., "Helper Virus-Free, Optically Controllable, and Two-Plasmid-Based PRoduction of Adeno-Associated Virus Vectors of Serotypes 1 to 6" Molecular Therapy; Jun. 2003; vol. 7, No. 6 pp. 839-850.

Tak, P. "Examination of the Synovium Fluid" Rheumatoid Arthritis, Chapter 5.

Vervoordeldonk, M, et al. "Gene Therapy in Rheumatic Disease" Best Practuce and Research Clinical Rheumatology, 2001, vol. 15, No. 5, pp. 771-788.

Hirata, R. et al. "Design and Packaging of Adeno-Associated Virus Gene Targeting Vectors" Journal fo Virology, May 2000, vol. 74, No. 10, pp. 4612-4620.

Pan, R. Y. et al. "Disease-Inducible Transgene Expression from a Recombiant Adeno-Associated VIrus Vector in a Rat Arthritis Model" Journal of Virology, Apr. 1999, vol. 73, No. 4, pp. 3410-3417.

Ghivizzani, S. et al. "Direct Gene Delivery Strategies for the Treatment of Rheumatoid Arthritis" Therapeutic Focus, Mar. 2001, vol. 6 No. 5, pp. 259-267.

Pan, R. Y. et al. "Disease-Inductible Transgene Expression from a Recombinant Adeno-Assocated Virus Vector ina Rat Arthritis Model" Journal of Virology, Apr. 1999, vol. 73, No. 4, pp. 3410-3417.

Chiorini, J. et al. "Cloning and CHaracterization of Adeno-Associated VIrus Type 5" Journal of Virology, Feb. 1999, vol. 73, No. 2, pp. 1309-1319.

Croxford J. L. et al. "Gene Therapy for Chronic Relapsing Experimental Allergic Encephalomyelitis Using Cells Expressing a Novel Soluble p75 Dimeric TNF Receptor" The Journal of Immunology, 2000, vol. 164, pp. 2776-2781.

Grimm, D. "Production Methods for Gene Transfer Vectors Based on Adeno-Associated Virus Serotypes" Methods, 2002, vol. 28, pp. 146-157.

Boyle DL, et al. "Intra-Articular IL-4 Gene Therapy in Arthritis: Anti-Inflammatory Effect and Enhanced Th2 Activity" Gene Therapy, 1999, vol. 6, pp. 1911-1918.

Tsao P. et al. "Rapid Communication—The Effect of Dexamethasone on the Expression of Activated NF-κB in Adjuvant Arthritis" Clinical Immunology and Immunopathology, May 1997, vol. 83, No. 2, pp. 173-178.

Miagkov, A. et al. "NF-κB Activation Provides te Potential Link Between Inflammation and Hyperplasia in the Arthritic Joint" Medical Sciences—Proc. Natl. Acad. Sci. USA, Nov. 1998, vol. 95, pp. 13859-13864.

Xiao, X et al. "Efficient Long-Term Gene Transfer in MUscle Tissue of Immunocompetent Mice by Adeno-Associated Virus Vector" Journal of Virology, Nov. 1996, vol. 70, No. 11, pp. 8098-8108.

Gerlag, D. et al. "The Effect of a T Cell-Specific NF- κB Inhibitor on in Vitro Cytokine Production and Collagen-Induced Arthritis", The Journal of Immunology, 2000, vol. 165, pp. 1652-1658.

Hsieh, C. L. et al. "Improved Gene Expression by a MOdified Bicistronic Retroviral Vector" Biochemical and Biophysical Research Communications, Sep. 25, 1995, vol. 214, No. 3 pp. 910-917.

Cominelli F. et al. "Rabbit Interleukin-1 Receptor Antagonist—Coning, Expression, Functional, Characterization, and Regulation During Intestinal Inflammation" The Journal of Biological Chemistry, Mar. 4, 1994, vol. 269, No. 9, pp. 6962-6971.

Delgado, M. "VIP: A Very Important Peptide in T Helper Differentiation" Trends in Ummunology, May 2003, vol. 24, No. 5, pp. 221-224.

St. Clair, M. et al. "Inhibition by Ganciclovir of Cell Growth and DNA Synthesis of Cells Biochemically Transformed with Herpesvirus Genetic Information" Antimicrobial Agents and Chemotherapy, Jun. 1987, vol. 31, No. 6, pp. 844-849.

Zolothukhin, S. et al. "A 'Humanized' Green Fluorescent Protein cDNA Adapted for High-Level Expression in Mammalian Cells" Journal of Virology, Jul. 1996, vol. 70, No. 7, pp. 4646-4654.

Zolotukhin, S. et al. "Recombinant Adeno-Associated Virus Purification Using Novel Methods Improves Infectious Titer and Yield" Gene Therapy, 1999, vol. 6, pp. 973-985.

Apparailly et al., Human Gene Therapy. 16:426-434 (2005).
Burger et al., Mole Ther. 10:302-317 (2004).
Chiorini et al., Journal fo Cirology, 73:139-1319 (1999).
DiPasquale et al., Nat Med. 9:1306-1312 (2003).
Rutledge et al., Journal of Virology. 72:309-319 (1998).
Vite et al., Gene Ther. 10:1874-1881 (2003).
Zabner et al., Journal of Virology. 74:3852-3858 (2000).

\* cited by examiner

Fig 6a
Fig 6b
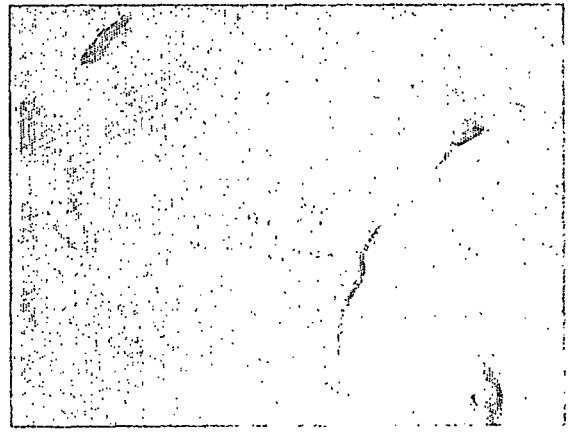

SEQUENCE LISTING

```
<160> NUMBER OF SEQ ID NOS: 4

<210> SEQ ID NO 1
<211> LENGTH: 30
<212> TYPE: DNA
<213> ORGANISM: artificial
<220> FEATURE:
<223> OTHER INFORMATION: primer

<400> SEQUENCE: 1
gcatcgagct gggtaataag cgttggcaat                                          30

<210> SEQ ID NO 2
<211> LENGTH: 30
<212> TYPE: DNA
<213> ORGANISM: artificial
<220> FEATURE:
<223> OTHER INFORMATION: primer

<400> SEQUENCE: 2
gacaccagac caactggtaa tggtagcgac                                          30

<210> SEQ ID NO 3
<211> LENGTH: 19
<212> TYPE: DNA
<213> ORGANISM: artificial
<220> FEATURE:
<223> OTHER INFORMATION: primer

<400> SEQUENCE: 3
aatgggcggt aggcgtgta                                                      19

<210> SEQ ID NO 4
<211> LENGTH: 22
<212> TYPE: DNA
<213> ORGANISM: artificial
<220> FEATURE:
<223> OTHER INFORMATION: primer

<400> SEQUENCE: 4
aggcgatctg acggttcact aa                                                  22
```

AAV VECTORS FOR IN VIVO GENE THERAPY OF RHEUMATOID ARTHRITIS

FIELD OF THE INVENTION

The present invention relates to the field of adeno-associated virus (AAV) based gene therapy, in particular in vivo gene therapy, of rheumatoid arthritis (RA). The invention provides recombinant AAV virions being highly efficient in delivering genes encoding therapeutic proteins, such as anti-inflammatory proteins or proteins inhibiting NF-κB activity, to the joints, and methods for using such virions in in vivo or in ex vivo gene therapy.

BACKGROUND OF THE INVENTION

Rheumatoid arthritis (RA) is a progressive destructive disorder that targets primarily the joints and is characterized by the hyperproliferation of synovial tissue and the infiltration of blood-derived cells resulting in the progressive erosion of the cartilage and bone. The incidence of RA has been reported to be around 30 per 100,000 population, and it may affect any age group from children to the elderly. The disease prevalence is about 1 percent worldwide. Thus, there are about 150,000 RA patients in the Netherlands only. The peak onset is between the ages of 30 and 55 and, because of the consistently higher rates in females, the prevalence of RA in females over 65 years is up to 5 percent.

RA is associated with a high degree of economic loss, morbidity, and early mortality. As an example, almost 80 percent of patients in one center were severely disabled after 20 years' follow-up; an additional one third had died. Patients with RA that require hospital care have at least a twofold increased mortality when compared to normals, and more severe RA is associated with higher mortality rates. The excess mortality in severe RA has been compared to that of three-vessel coronary artery disease or stage IV Hodgkin's disease.

An appreciation of the pathogenic mechanisms of RA and the poor outcomes with conventional therapy has led to the recent concept of aggressive treatment of newly diagnosed or early disease to suppress ongoing inflammation and prevent joint injury. Drug therapy is the mainstay of treatment for all patients except for those in clinical remission. Such therapy should be instituted with the goals of treating each patient sufficiently to induce a remission and preventing further loss of joint tissues or function in daily activities. In addition to conventional therapy with disease-modifying antirheumatic drugs, novel approaches aimed at TNF-α blockade have successfully entered the clinic. It is now possible to reach 20% improvement in about 70% of the RA patients using this approach. The majority of these American College of Rheumatology (ACR) 20% responders, however, will still have some actively inflamed joints. About 30% of the patients will not respond to TNF-α blockade with regard to arthritis activity.

Intra-articular corticosteroids are an important mainstay of the treatment of symptomatic synovitis in patients with RA. Especially when there is isolated arthritis activity under systemic antirheumatic therapy, as may occur in most patients, there is an indication for local treatment. However, not all patients will respond to the use of corticosteroids and its use is limited by side-effects.

The pathology of RA extends throughout the synovial joint. In contrast to the acellular nature of normal synovial fluid, RA synovial fluid is enriched predominantly with neutrophils, but macrophages, T-lymphocytes and dendritic cells are also present (Tak, P. P. Examination of the synovium and synovial fluid. In: Firestein G S, Panayi G S, Wollheim F A, editors. Rheumatoid arthritis. Frontiers in pathogenesis and treatment. New York: Oxford University Press, Inc., 2000: 55-68). The increase in cellularity is most obvious in the synovial membrane, which becomes infiltrated by cells recruited from the blood. The lining layer of the joint is increased from 1-2 cells to 6-8 cells thick and consists mainly of activated intimal macrophages and fibroblast-like synoviocytes. Alterations in the normal biology of synoviocytes are important in the development and maintenance of the pathologic process associated with RA, including invasion and destruction of articular cartilage and bone. In addition to the production of soluble mediators such as elastase and collagenase, synoviocytes mediate this pathophysiologic process by the expression of cell surface proteins, which are involved in the recruitment and activation of lymphocytes and macrophages within rheumatoid synovium. Synoviocytes are easily reached via the intra-articular space, are relatively long-lived, and thus represent an ideal target for gene therapy strategies (Chernajovsky, Y. et al., 1998, Drug Aging 12:29-41; Robbins, P. D. et al., 1998, Springer Semin. Immunopathol. 20:197-209).

In addition, the localized nature of the joint makes in vivo gene therapy very attractive. Many cellular and molecular interactions in the rheumatoid synovium are maintained and modulated by cytokines. A consistent finding in RA has been the abundance of fibroblast- and macrophage-derived proinflammatory cytokines such as IL-1, TNFα, and IL-18 in the rheumatoid synovium. The naturally occurring IL-1 and TNFα inhibitors, IL-1 receptor antagonist (IL-1RA) and the soluble TNFα receptors p55 and p75 are produced in parallel with their counterparts. For IL-18 an IL-18 binding protein is purified. Therapies providing excess recombinant cytokine inhibitors may shift the balance in RA towards an anti-inflammatory state. Clinical efficacy of anti-TNF-α and anti-IL-1 directed approaches emphasize that certain cytokines are appropriate targets for gene therapy. Another approach could be the directed overexpression of biologically active anti-inflammatory proteins (e.g. IL-4, IL-10, IL-13, and IFN-β) by synoviocytes to inhibit the inflammatory cascade (Boyle, D. L. et al., 1999, Gene Ther. 6:1911-1918).

NF-κB is clearly one of the most important regulators of pro-inflammatory gene expression (Tak, P. P. and Firestein, G. S., 2001, J. Clin. Invest. 107(1): 7-11). Synthesis of cytokines, such as TNF-α, IL-1β, IL-6, and IL-8 is mediated by NF-κB, as is the expression of Cox-2. Aupperle et al. (1999, J. Immunol. 163: 427-433) recently studied the role of IKK in primary fibroblast-like synoviocytes isolated from synovium of patients with RA and osteoarthritis. In both groups, immunoreactive IKK protein is abundant in these cells, and IKK-α and IKK-β are constitutively expressed at the mRNA level. IKK function in these cells can be greatly enhanced by TNF-α and IL-1, leading to degradation of endogenous IκB-α and nuclear translocation of NF-κB. Activation of this pathway and the consequent induction of IL-6, IL-8, ICAM-1, and collagenase-1 expression, depends specifically on IKK-β (Aupperle, K. R. et al., 1999, J. Immunol. 163: 427-433). Thus, transfection with adenoviral constructs encoding an IKK-β dominant negative mutant prevents TNF-α-mediated NF-κB nuclear translocation and pro-inflammatory gene expression in synoviocytes, whereas dominant negative IKK-α mutant has no effect (Aupperle, K. R. et al., 1999, J. Immunol. 163: 427-433).

Animal models of inflammatory arthritis support the notion that NF-κB activation plays a pathogenic role in vivo. For instance, increased synovial NF-κB binding precedes the development of clinical joint involvement in murine collagen-induced arthritis and gradually increases during the evolution of disease (Han, Z. N., et al. 1998, Autoimmunity 28: 197-208). Much of this binding activity appears to be due to p50, which has been implicated in collagenase-3 transcription and could contribute, along with locally activated AP-1, to extracellular matrix resorption. Synovial NF-κB activation also occurs within a few days after immunization in rat adjuvant arthritis (Tsao, P. W. et al. 1997, Clin. Immunol. Immunopathol. 83: 173-178). Selective activation of NF-κB in normal rats by intra-articular transfer of a functional IKK-β gene, leads to synovial inflammation and clinical signs of arthritis (Tak, P. P. et al., 2001, Arthritis Rheum. 44(8): 1897-907). Conversely, reduction of NF-κB nuclear translocation and clinical synovitis was observed in adjuvant arthritis in rats after an intra-articular injection with a dominant negative adenoviral IKK-β construct (Tak, P. P. et al., 2001, Arthritis Rheum. 44(8): 1897-907). The central role of NF-κB in inflammation has also been shown in rats with streptococcal cell wall-induced arthritis (Miagkov, A. V. et al., 1998, Proc. Natl. Acad. Sci. U.S.A. 95: 13859-13864) and in mice with collagen-induced arthritis (CIA) (Gerlag, D. M. et al., 2000, J. Immunol. 165: 1652-1658; Han, Z. N. et al. 1998, Autoimmunity 28:197-208).

Hence, various strategies aimed at increasing local production of anti-inflammatory proteins or aimed at inhibition of NF-κB activity in the synovial compartment by in vivo gene therapy hold great promise for the treatment of RA.

In order to enable sustained local production of effective doses of therapeutic proteins in the joint, in particular in the rheumatoid synovium, an efficient gene delivery system needs to be developed. A range of different viral and non-viral vectors exist, such as adenoviral vectors, adeno-associated virus vectors, retroviral vectors, herpes virus vectors, liposomes, DNA vaccination and the like (see Vervoordeldonk M. J. B. M and Tak P. P. 2001, Best Practice & Research Clinical Rheumatology Vol. 15 (5): 771-788). To date mainly adenoviral vectors have been tested as vectors for gene delivery. However, their episomal nature limits the duration of the gene expression, thereby making them not very suitable for the treatment of arthritis, where long-term gene expression is required.

Another disadvantage of adenoviral vectors is the presence of viral proteins, which may elicit an immune response in the host.

Adeno-associated viral vectors (AAV), on the other hand, have been shown (in some tissues) to integrate into the genome of the target cell (Hirata et al. 2000, J. of Virology 74:4612-4620), allowing long-term transgene expression in transduced cells. Adeno-associated virus is a helper-dependent DNA parvovirus, which is not associated with disease in humans or mammals (for review see Berns and Bohensky, 1987, Advances in Virus Research, Academic Press Inc, 32:243-307). Recombinant AAV vectors have been shown to be able to transfect a range of different cell types, such as hematopoietic cells, respiratory epithelial cells and neurons. However, for many cell types (such as for example synovial cells, but also many others) it remains unclear whether or not they can be transfected at all or efficiently by AAV vectors. Pan et al. (J. of Virology 1999, Vol 73, 4: 3410-3417) have been able to transfect rat synoviocytes showing symptoms of lipopolysaccharide induced arthritis using rAAV vectors, but they found that transgene expression diminished when inflammation subsided. Moreover, the literature reports widely divergent results from experiments attempting in vivo gene delivery to joints with AAV based vectors (Ghivizanni et al. 2000, Drug Discov. Today 6:259-267).

A complicating factor is that AAV serotypes differ in cellular tropism. WO99/61601 for example shows that AAV5 based vectors transduced certain cell types (cultured airway epithilial cells, cultured striated muscle cells and cultured human umbilical vein endothelial cells) at a higher efficiency than AAV2. On the other hand, AAV5 was much more inefficient in transducing cultured cos cells, 293, HeLa, IB3 cells and MCF7 cell lines, while both AAV2 and AAV5 showed poor transduction efficiencies for NIH 3T3, skbr3 and t-47D cell lines.

Despite the availability of the above viral and non-viral gene delivery systems, to date no suitable vector system exists for effective delivery of genes (encoding therapeutic proteins) to the rheumatoid synovium of subjects suffering from rheumatoid arthritis. There remains, therefore, a need to generate a suitable in vivo and ex vivo gene delivery system to the synovium in order to enable effective treatment. The present invention provides such a gene delivery system.

SUMMARY OF THE INVENTION

The invention provides in one embodiment a method for delivering a nucleic acid molecule to a rheumatoid synovial cell in vivo, the method comprising the steps of (a) providing a recombinant AAV virion (rAAV) comprising capsid proteins of AAV serotype 5 or AAV serotype 2, wherein the rAAV virion comprises a rAAVX vector, the rAAVX vector comprising an expression element operably linked to a nucleic acid sequence; and, (b) bringing the rAAV virion into contact with the synovial cell, whereby transduction of the rAAVX vector results in expression of the nucleic acid sequence in the transduced synovial cells.

In another embodiment the invention provides a method for treating rheumatoid joints using the rAAV virions of the invention is provided. The method preferably comprises the steps of (a) establishing diagnosis of rheumatoid arthritis of a joint; (b) transducing rheumatoid synovial cells of the joint using a therapeutically effective amount of a pharmaceutical composition comprising a pharmaceutically acceptable excipient and rAAV virions comprising capsid proteins of AAV serotype 5 or AAV serotype 2, wherein the rAAV virions comprise a rAAVX vector comprising a nucleotide sequence encoding at least one therapeutic protein (or peptide) and, (c) optionally repeating step (b) after a certain period of time.

In an alternative embodiment of the treatment, the method comprises transducing rheumatoid synovial cells ex vivo using a rAAV virion of the invention, optionally selecting the transduced cells, administering the transduced cells to a rheumatoid joint of a subject, and optionally repeating the administration after a certain period of time.

In another embodiment of the invention a recombinant AAV virion is provided whereby the virion comprises capsid proteins of AAV serotype 5 or AAV serotype 2, whereby the rAAV virion comprises a rAAVX vector, wherein the rAAVX vector comprises an expression element operably linked to a nucleic acid sequence encoding a therapeutic protein effective against rheumatoid arthritis.

DESCRIPTION OF THE FIGURES

FIG. 6: rAAV 5 mediates gene transfer to human fibroblast-like synoviocytes (FLS) in vitro. Human FLS isolated from synovial biopsies from RA patients were transduced with AAV5.GFP. Forty-eight hours after transfection the cells were fixated fluorescent microscopy. A: fluorescent cells, B: phase contrast photograph.

DETAILED DESCRIPTION OF THE INVENTION

A. General Definitions

Figure 1:
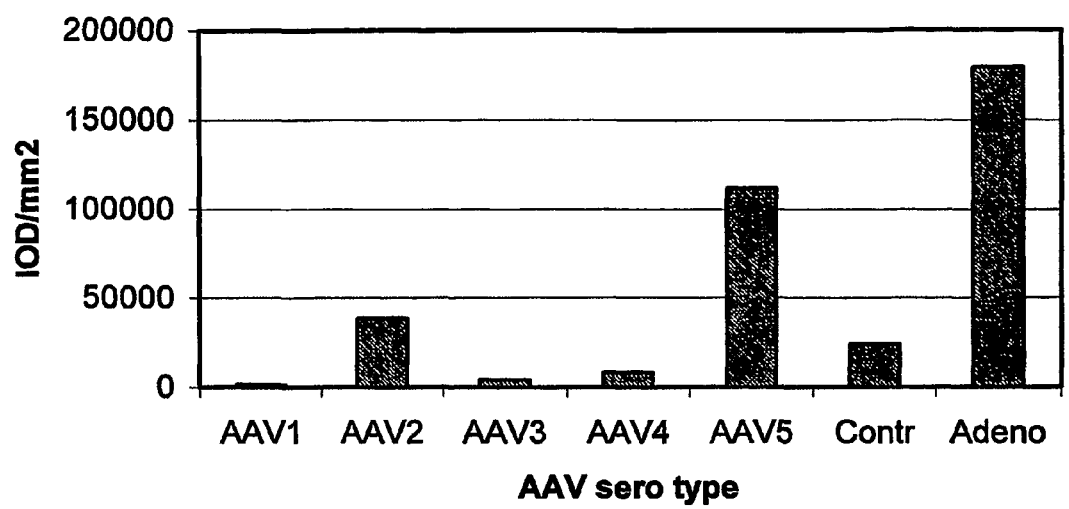
FIG. 1 χ-Gal (5-bromo-4-chloro-3-indolyl-β-D-galactopyranosidase) staining (results of quantified digital image analysis) of direct in-situ staining of frozen sections of rat joints treated transduced with rAAV1, rAAV2, rAAV3, rAAV4, rAAV5, a control vector and adenovirus expressing the gene for LacZ.

"Gene" or "coding sequence" refers to a DNA or RNA region (the transcribed region) which "encodes" a particular protein. A coding sequence is transcribed (DNA) and translated (RNA) into a polypeptide when placed under the control of an appropriate regulatory region, such as a promoter. A gene may comprise several operably linked fragments, such as a promoter, a 5'leader sequence, a coding sequence and a 3'nontranslated sequence, comprising a polyadenylation site. A chimeric or recombinant gene is a gene not normally found in nature, such as a gene in which for example the promoter is not associated in nature with part or all of the transcribed DNA region. "Expression of a gene" refers to the process wherein a gene is transcribed into an RNA and/or translated into an active protein.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically or developmentally regulated. A "tissue specific" promoter is only active in specific types of tissues or cells.

As used herein, the term "operably linked" refers to two or more nucleic acid or amino acid sequence elements that are physically linked in such a way that they are in a functional relationship with each other. For instance, a promoter is operably linked to a coding sequence if the promoter is able to initiate or otherwise control/regulate the transcription and/or expression of a coding sequence, in which case the coding sequence should be understood as being "under the control of" the promoter. Generally, when two nucleic acid sequences are operably linked, they will be in the same orientation and usually also in the same reading frame. They will usually also be essentially contiguous, although this may not be required.

The terms "signal sequence", "signal peptide" and "secretory leader" are used interchangeably and refer to a short (usually about 15-60 amino acids), continuous stretch of amino acids usually present at the amino-terminus of secreted and membrane-bound polypeptides and that directs their delivery to various locations outside the cytosol. Thus, specific sorting or targeting signals, which include signal sequences, may direct the delivery of polypeptides into the nucleus, ER, mitochondria, peroxisomes, etc. Signal sequences usually contain a hydrophobic core of about 4-15 amino acids, which is often immediately preceded by a basic amino acid. At the carboxyl-terminal end of the signal peptide there are a pair of small, uncharged amino acids separated by a single intervening amino acid that defines the signal peptide cleavage site. von Heijne, G. (1990) J. Membrane Biol. 115: 195-201. Despite their overall structural and functional similarities, native signal peptides do not have a consensus sequence.

"Gene delivery" or "gene transfer" refers to methods for reliable introduction of recombinant or foreign DNA into host cells. The transferred DNA can remain non-integrated or preferably integrates into the genome of the host cell. Gene delivery can take place for example by transduction, using viral vectors, or by transformation of cells, using known methods, such as electroporation, cell bombardment and the like.

"Vector" refers generally to nucleic acid constructs suitable for cloning and expression of nucleotide sequences. The term vector may also sometimes refer to transport vehicles comprising the vector, such as viruses or virions, which are able to transfer the vector into and between host cells.

"rAAV vector" as used herein refers to a recombinant vector derived from an adeno-associated virus serotype, such as AAV1, AAV2, AAV3, AAV4, AAV5 and others. rAAV vectors have one or preferably all wild type AAV genes deleted, but still comprise functional ITR nucleic acid sequences. Functional ITR sequences are necessary for the replication, rescue and packaging of AAV virions. The ITR sequences may be wild type sequences or substantially identical sequences (as defined below) or may be altered by for example in insertion, mutation, deletion or substitution of nucleotides, as long as they remain functional.

"rAAV vector" as used herein refers to a recombinant AAV vector comprising the ITR nucleic acid sequences of any of the AAV serotypes, or nucleic acid sequences being substantially identical to the particular AAV serotype wild type ITR sequences, as long as they remain functional. Nucleotide sequences of choice are inserted between the AAV ITR sequences, for example expression constructs comprising an expression regulatory element operably linked to a coding sequence and a 3' termination sequence. The term "rAAVX vector" as used herein refers to a recombinant AAV vector comprising the ITR nucleic acid sequences of the AAVX serotype, or nucleic acid sequences being substantially identical to the AAVX serotype wild type ITR sequences, as long as they remain functional. The term "rAAV5 vector" or "rAAV2 vector" is thus used to indicate a rAAV5 or rAAV2 vector comprising respectively the ITR nucleic acid sequences of AAV serotype 5 or serotype 2, or nucleic acid sequences substantially identical thereto.

"AAV virion" refers to a complete virus particle, such as for example a wild type AAV virion particle, which comprises single stranded genome DNA packaged into AAV capsid proteins. The single stranded nucleic acid molecule is either sense strand or antisense strand, as both strands are equally infectious. A "rAAV virion" refers to a recombinant AAV virus particle, i.e. a particle which is infectious but replication defective. It is composed of an AAV protein shell and comprises a rAAV vector. In the context of the present invention the protein shell may be of a different serotype than the rAAV vector. An AAV virion of the invention may thus be composed a protein shell, i.e. the icosahedral capsid, which comprises capsid proteins (VP1, VP2, and/or VP3) of one AAV serotype, e.g. AAV serotype 5, whereas the rAAV vector contained in that AAV5 virion may be any of the rAAVX vectors described above, including a rAAV5 vector. An "rAAV5 virion" thus comprises capsid proteins of AAV serotype 5, while e.g. a rAAV2 virion comprises capsid proteins of AAV serotype 2, whereby either may comprise any of rAAVX vectors of the invention.

"AAV helper functions" generally refers to the corresponding AAV functions required for rAAV replication and packaging supplied to the rAAV virion or rAAV vector in trans. AAV helper functions complement the AAV functions which are missing in the rAAV vector, but they lack AAV ITRs (which are provided by the rAAV vector). AAV helper functions include the two major ORFs of AAV, namely the rep coding region and the cap coding region or functional substantially identical sequences thereof. Rep and Cap regions are well known in the art, see e.g. Chiorini et al. (1999, J. of Virology, Vol 73(2): 1309-1319) or U.S. Pat. No. 5,139,941, incorporated herein by reference. The AAV helper functions can be supplied on a AAV helper construct. Introduction of the helper construct by into the host cell can occur e.g. by transformation or transduction prior to or concurrently with the introduction of the rAAV vector. The AAV helper constructs of the invention may thus be chosen such that they produce the desired combination of serotypes for the rAAV virion's capsid proteins on the one hand and for the rAAVX vector replication and packaging on the other hand.

"AAV helper virus" provides additional functions required for AAV replication and packaging. Suitable AAV helper viruses include adenoviruses, herpes simplex viruses (such as HSV types 1 and 2) and vaccinia viruses. The additional functions provided by the helper virus can also be introduced into the host cell via vectors, as described in U.S. Pat. No. 6,531,456 incorporated herein by reference.

A "transgene" is herein defined as a gene that has been newly introduced into a cell, i.e. a gene that does not normally occur in the cell. The transgene may comprise sequences that are native to the cell, sequences that in naturally do not occur in the cell and it may comprise combinations of both. A transgene may contain sequences coding for one or more proteins that may be operably linked to appropriate regulatory sequences for expression of the coding sequences in the cell. Preferably, the transgene is integrated into the host cell's genome.

"Transduction" refers to the delivery of a DNA molecule into a recipient host cell by an AAV virion. For example, transduction of a target cell by a rAAV virion of the invention leads to transfer of the rAAVX vector contained in that virion into the transduced cell. "Host cell" or "target cell" refers to the cell into which the DNA delivery takes place, such as the synoviocytes of a subject. AAV virions are able to transduce both dividing and non-dividing cells.

"Subjects" means any member of the class mammalia, including without limitation humans, non-human primates, farm animals, domestic animals and laboratory animals.

The term "intra-articular" refers to the interior of a joint, e. g., knee, elbow, shoulder, ankle, wrist, etc. Thus, an intra-articular injection is an injection into the space between the bones of a joint. In the knee, "intra-articular" refers to the space between the femur and the tibia, behind and surrounding the patella.

The term "substantial identity" means that two peptide or two nucleotide sequences, when optimally aligned, such as by the programs GAP or BESTFIT using default parameters, share at least 80 percent sequence identity, preferably at least 90 percent sequence identity, more preferably at least 95 percent sequence identity or more (e.g., 99 percent sequence identity). GAP uses the Needleman and Wunsch global alignment algorithm to align two sequences over their entire length, maximizing the number of matches and minimizes the number of gaps. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992).

The term "comprising" is to be interpreted as specifying the presence of the stated parts, steps or components, but does not exclude the presence of one or more additional parts, steps or components. A nucleic acid sequence comprising region X, may thus comprise additional regions, i.e. region X may be embedded in a larger nucleic acid region.

B. Embodiments of the Invention

AAV is a non-enveloped DNA virus, which requires a helper virus to replicate. Recombinant AAV vectors have a number of important advantages over other vectors as they are non-pathogenic in humans, immunologically inert and allow long-term gene expression in vivo. Their capacity to mediate expression of therapeutically relevant genes is now well established in several experimental models of arthritis. Although an increasing number of AAV serotypes has been identified, all studies so far have been performed with serotype 2 (AAV2). Different serotypes have different virion shell proteins and, as a consequence, vary in their tropism.

The present inventors have surprisingly found that AAV virions of different serotypes vary considerably in their transduction efficiency when used as AAV vectors for in vivo delivery of genes to the arthritic joints, in particular to the synovium. When comparing transduction efficiencies of recombinant virions comprising rAAV vectors based on five different AAV serotypes (AAV1 to AAV5) encoding the reporter genes murine secreted alkaline phosphatase (mSEAP) or E. coli beta-galactosidase (beta-Gal), in two different animal models of arthritis (mouse and rat), it was surprisingly found that in vivo gene transfer was far more efficient with AAV5 virions than with the virions based on serotypes AAV1 to AAV4. The inventors have thus been able to provide an efficient gene delivery system to synovial cells, The invention therefore discloses therapeutic methods for the treatment of rheumatoid arthritis, in particular the treatment of rheumatoid joint, based on in vivo gene therapy of the rheumatoid synovium.

It is one embodiment of the invention to provide methods for locally delivering nucleic acid molecules to arthritic joints, in particular to the rheumatoid synovium. In particular, the methods provided enable the efficient transduction of nucleic acid molecules encoding therapeutic proteins into rheumatoid synovial cells and tissues in a therapeutically effective amount and for a therapeutically effective time period. The methods of the invention provide improved, sustained (long term) high level expression of therapeutic proteins in target cells. Without limiting the scope of the invention, it is especially the high transduction efficiency of the rAAV5, and to a lesser extent the AAV2 virions, in combination with the rAAV vectors of the invention, which enables efficient vivo gene delivery. Although rAAV virions comprising capsid proteins of both AAV serotype 5 and 2 may advantageously be used in the present invention, rAAV virions comprising capsid proteins of AAV serotype 5 (rAAV5 virions) are thus most preferred for use in the methods and compositions of the invention.

The methods of the invention comprise the steps of (a) providing a recombinant AAV virion (rAAV) comprising capsid proteins of AAV serotype 5 or AAV serotype 2, wherein the rAAV virion comprises a rAAVX vector, the rAAVX vector comprising an expression element operably linked to a nucleic acid sequence; and, (b) bringing the rAAV virion into contact with the synovial cell, whereby transduction of the rAAVX vector results in expression of the nucleic acid sequence in the transduced synovial cells. Preferably in the method, the nucleic acid sequence is delivered to the synovial cell in vivo, by local administration of the rAAV virion to a rheumatoid joint of a subject. Preferably, administration of the rAAV virion is by injection into the joint, more preferably by injection into the synovial compartment. Alternatively, in the method, the rAAV virion is brought into contact with synovial cells or cell cultures comprising synovial cells ex vivo, and whereby optionally the transduced cells are selected. The alternative method may further comprises the step of administering the transduced cells to a rheumatoid joint of a subject, whereby, preferably administration of the transduced cells is by injection into the joint, preferably by injection into the synovial compartment. Preferably in these methods the expression of the nucleic acid sequence in the in vivo or ex vivo transduced synovial cell results in a reduction of symptoms of arthritis of the joint.

The recombinant AAV virion, including one of the rAAVX vectors, is produced using methods known in the art, as described in Pan et al. (J. of Virology 1999, Vol 73(4):3410-3417) and Clark et al. (Human Gene Therapy, 1999, 10:1031-1039), incorporated herein by reference. In short, the methods generally involve (a) the introduction of the rAAV vector into a host cell, (b) the introduction of an AAV helper construct into the host cell, wherein the helper construct comprises the viral functions missing from the rAAV vector and (c) introducing a helper virus into the host cell. All functions for rAAV virion replication and packaging need to be present, to achieve replication and packaging of the rAAV vector into rAAV virions. The introduction into the host cell can be carried out using standard virological techniques and can be simultaneously or sequentially. Finally, the host cells are cultured to produce rAAV virions and are purified using standard techniques such as CsCl gradients (Xiao et al. 1996, J. Virol. 70: 8098-8108). Residual helper virus activity can be inactivated using known methods, such as for example heat inactivation. The purified rAAV virion is then ready for use in the methods. High titres of more than $10^{12}$ particles per ml and high purity (free of detectable helper and wild type viruses) can be achieved (Clark et al. supra and Flotte et al. 1995, Gene Ther. 2: 29-37).

The rAAVX vector comprises at least the nucleotide sequences of the inverted terminal repeat regions (ITR) of one of the AAV serotypes, or nucleotide sequences substantially identical thereto, and at least one nucleotide sequence encoding a therapeutic protein (under control of a suitable regulatory element) inserted between the two ITRs.

The complete genome of AAV5 and other AAV serotypes has been sequenced (Chiorini et al. 1999, J. of Virology Vol. 73, No. 2, p 1309-1319) and the nucleotide sequence is available in GenBank (Accession No. AF085716). The ITR nucleotide sequences of AAV5 are thus readily available to a skilled person. They can be either cloned or made by chemical synthesis as known in the art, using for example an oligonucleotide synthesizer as supplied e.g. by Applied Biosystems Inc. (Fosters, Calif., USA) or by standard molecular biology techniques. The ITRs can be cloned from the AAV viral genome or excised from a vector comprising the AAV ITRs. The ITR nucleotide sequences can be either ligated at either end to the nucleotide sequence encoding one or more therapeutic proteins using standard molecular biology techniques, or the wild type AAV sequence between the ITRs can be replaced with the desired nucleotide sequence.

Preferably, the rAAV vector does not comprise any nucleotide sequences encoding viral proteins, such as the rep (replication) or cap (capsid) genes of AAV. The rAAV vector may further comprise a marker or reporter gene, such as a gene for example encoding an antibiotic resistance gene, a fluorescent protein (e.g. gfp) or a gene encoding a chemically, enzymatically or otherwise detectable and/or selectable product (e.g. lacZ, aph, etc.) known in the art.

The rAAV vector further comprises a promoter sequence operably linked to the nucleotide sequence encoding a therapeutic protein. Suitable promoter sequences are promoters which confer expression in cells of the rheumatoid synovium, such as in intimal macrophages and/or in fibroblast-like synoviocytes and/or other synovial cells such as, but not limited to, T-cells. Suitable promoters are for example the promoters of genes known to be expressed in synovial cells, such as the CMV promoter (cytomegalovirus), the promoter of the IL-6 gene or the SV40 promoter, and others, as readily determined by a skilled person.

A suitable 3' non-translated sequence may also be operably linked to the nucleotide sequence encoding the therapeutic protein. Suitable 3' non-translated regions may be those naturally associated with the nucleotide sequence or may be derived from different genes, such as for example the bovine growth hormone 3' non-translated region (BGH polyA) sequence.

The total size of the DNA molecule inserted into the rAAV vector between the ITR regions is generally smaller than 5 kilobases (kb) in size. It is also envisaged that the rAAV vector comprises nucleotide sequences encoding two therapeutic proteins (e.g. therapeutic proteins having a synergistic effect). These may either comprise a suitable promoter and suitable 3'nontranslated region each, or they may be linked by an IRES (internal ribosome entry sites) element, providing a bicistronic transcript under control of a single promoter. Suitable IRES elements are described in e.g. Hsieh et al. (1995, Biochemical Biophys. Res. Commun. 214:910-917).

Optionally, additional nucleotide sequences may be operably linked to the nucleotide sequence(s) encoding the therapeutic protein, such as nucleotide sequences encoding signal peptides (e.g. for targeting transport of the peptide to the extracellular space), nuclear localization signals, expression enhancers, and the like.

A "therapeutic protein" as used herein refers to a protein, which has a therapeutic effect on rheumatoid arthritis when administered locally to the rheumatoid joint (in particular to the synovium) in an effective amount (or dosage). Suitable therapeutic proteins are for example cytokine inhibitors such as interleukin-1 (IL-1, March et al, 1985, Nature 315:641-647) or TNFα inhibitors, cytokine receptor antagonists such as for example the interleukin-1 receptor antagonist IL-Ra (Cominelli et al. 1994, J. Biol. Chem. 269(9): 6962-6971), cytokine binding proteins such as IL18 binding protein (Im et al. 2002, J. Interferon Cytokine Res. 22(3): 321-328) or soluble cytokine receptors such as sTNFα receptor p55 or p75 (Croxford et al., 2000, J. of Immunology 164: 2776-2718) or the soluble IL-1 receptor. Also suitable are sequences encoding TNF alpha antibodies, as known in the art, for instance in U.S. Pat. No. 6,277,969 and sequences encoding anti-sense or RNA interference sequences for TNF alpha, known in the art per se, for instance in U.S. Pat. No. 6,046,319. Also suitable are proteins with anti-inflammatory activity, such as IL-4, IL-10, IL-13, IFN-β or VIP (Vasoactive intestinal peptide; Delgado, 2003, Trends Immunol. 24: 221-4). Further, dn-IKK-β (dominant negative IκB-kinase), which inhibits the activation of NF-κB, is a suitable protein to be used. A list of suitable proteins is provided in Vervoordeldonk and Tak, 2001 (supra):

| Gene product[a] | Comment |
| --- | --- |
| IL-IRA, IL-IsR, TNFsR | Blocks IL-I/TNF activity, improves inflammatory symptoms, prevents disease progression and joint destruction |
| IL-4, (v)IL-10, IL-13, IFN-β | Anti-inflammatory, opposes the production and effects of pro-inflammatory cytokines; inhibits Th-I activity |
| TGF-β | Immunosuppressive |
| Decoy oligonucleotides | Prevents binding of transcription factors on target genes |
| Dn-IKK-β | Inhibits activation of NF-κB |
| FasL, FADD, herpes thymidine kinase (followed by ganciclovir) | Induction of apoptosis |
| CTLA-4 | Inhibits co-stimulation of lymphocytes |

[a]IL-RA = interleukine-I receptor antagonist; IL-IsR = soluble IL-I receptor; TNFsR = soluble tumor necrosis factor receptor; vIL-10 = viral IL-10; IFN-β = interferon beta; TGF-β = transforming growth factor β; dn-IKK-β = dominant negative IκB-kinase β; NF-κB = nuclear factor κB; FADD = Fas-associated death domain protein Nucleotide sequences encoding these proteins are readily available to a skilled person. The sequences (both nucleotide and protein) can for example be found in databases, such as GenBank, SwissProt, and others, and clones comprising the sequences can mostly be obtained from depositories such as the American Type Culture Collection (ATCC). In a preferred embodiment the nucleotide sequences are of human origin, but they may also originate from other species. They may be cDNA or genomic DNA sequences. Nucleotide sequences encoding therapeutic proteins encompass naturally occurring or de novo synthetic sequences, as well as nucleotide sequences encoding therapeutically active fragments, mutated forms or modified polypeptides (referred to as "variants"). Variants can be easily generated and tested for the retention of functionality using methods known in the art, such as but not limited to amino acid substitutions or deletions, de novo chemical synthesis of peptides or mutagenesis- or gene-shuffeling techniques, hybridization techniques. Variants of the therapeutic peptides include peptides with amino acid sequences with at least 80, 90, 95 or 99% "substantial sequence identity" to the naturally occurring protein, which retain their therapeutic effectiveness, i.e. the ability to reduce or abolish the symptoms of rheumatoid arthritis in subjects.

The rAAV vectors of the invention may in addition to a nucleotide sequence encoding a therapeutic protein comprise a second or further nucleotide sequence that encodes a protein that provides for fail-safe mechanism that allows to cure a subject from the rAAV vector or from cells transduced therewith, if deemed necessary. Such a nucleotide sequence, often referred to as a suicide gene, encodes a protein that is capable of converting a prodrug into a toxic substance that is capable of killing the transgenic cells in which the protein is expressed. Suitable examples of such suicide genes include e.g. the *E. coli* cytosine deaminase gene or one of the thymidine kinase genes from Herpes Simplex Virus, Cytomegalovirus and Varicella-Zoster virus, in which case ganciclovir may be used as prodrug to kill the IL-10 transgenic cells in the subject (see e.g. Clair et al., 1987, Antimicrob. Agents Chemother. 31: 844-849).

The administration occurs preferably by rAAV vectors as described elsewhere herein. A "therapeutic effect" on rheumatoid arthritis, and in particular on the rheumatoid synovium, refers to a decrease in the typical symptoms, such as a decrease in inflammation of the synovial tissue and/or a decrease in cartilage and/or bone destruction of the joint. A decrease may also mean a slow down in progression of symptom development or a complete disappearance of symptoms. Symptoms, and thus also a decrease in symptoms, can be assessed using a variety of methods, to a large extent the same methods as used in diagnosis of rheumatoid arthritis, including clinical examination and routine laboratory tests. Such methods include both macroscopic and microscopic methods, as well as molecular methods, X-rays, biochemical, immunohistochemical and others. The methods may involve analysis of the whole joint (e.g. X-ray), or of parts thereof, such as extracted synovial fluid or biopsies of synovial tissue. Rheumatoid synovial fluid, which is in direct contact with the synovium and the articular cartilage, has a high diagnostic value and is easily accessible for aspiration (see Tak P. P., Rheumatoid Arthritis 2000:55-68, supra).

The therapeutically effective amount needed to achieve a therapeutic effect may vary, depending on the subject being treated (e.g. non-human mammal or human), the therapeutic protein(s) encoded (including the strength and specificity of the promoter, the integration site, etc.) and on the developmental stage and severity of the rheumatoid arthritis of the joint. There is large variation of synovial inflammation between individuals, joints and even within joints (Tak et al. 1997, Arthritis Rheum. 40: 217-225). Likewise, the therapeutically effective period of time (the time it takes until a therapeutic effect becomes detectable) may vary between individuals and between joints and depending on the transgene. Also, treatment may have to be repeated at later stages for effectiveness. A skilled person can easily determine the therapeutically effective amount by routine trial and error and by e.g. drawing dose-response curves. An administration of at least $10^3$ to $10^5$ rAAV virions, preferably at least $10^7$ or $10^8$ virions, more preferably $10^9$ to $10^{11}$ virions or more will be a suitable dose.

Preferably, the rAAV vector is stably integrated into the genome of the transduced cell and provides long term (at least 4-8 weeks, preferably at least 8-12 weeks, more preferably at least 6 months or life long) expression of the therapeutic protein.

Local (as opposed to systemic) administration to the arthritic joint refers in particular to local in vivo or ex vivo administration of the rAAV virions to the rheumatoid synovium, and in particular to synoviocytes. In vivo administration as used herein refers to the direct administration of the rAAV virions to the joint of the subject, for example by intra-articular injection. Ex vivo administration refers to the isolation of rheumatoid cells from the subject, followed by the administration of the rAAV virions to the isolated, cultured cells. The transduced cells expressing the therapeutic protein are then administered to the subject, by for example injection, reinplantation or reinfusion of the cells back into the joint of the subject. Local administration may be repeated after a number of weeks or months if necessary.

In a further embodiment the invention provides a method for delivering a nucleic acid molecule to rheumatoid synovial cells ex vivo, the method comprising the steps of (a) providing a recombinant AAV virion (rAAV) comprising capsid proteins of AAV serotype 2 or more preferably AAV serotype 5, wherein the rAAV virion comprises a rAAVX vector, the rAAVX vector comprising an expression element operably linked to a nucleic acid sequence; (b) administering the rAAV virion to synovial cells, or cell cultures comprising synovial cells, whereby transduction results in expression of the nucleic acid molecule in the transduced cells; (c) optionally, selecting the transduced cells; and (d) administering the transduced cells or cells comprising the transduced cells to the rheumatoid joint of a subject.

Selection or enrichment of the tranduced cells prior to re-administration to the joint from which the cells originated can be done using known methods. The subject from which the cells or cell cultures are obtained in step (b) need not be the same subject to which the transduced cells are re-administered in step (d), i.e. the cells may be autologous (from the same subject) or non-autologous (from a different subject).

The rAAV5 virions of the invention may also be formulated into pharmaceutical compositions, so that instead of administering the rAAV virions directly to the joint, the pharmaceutical composition is administered locally in vivo, e.g. by injection or microinjection. The pharmaceutical composition comprises sufficient rAAV virions and additional pharmaceutically acceptable excipients, such as but not limited to water, saline, glycerol or ethanol. Additional substance may be present, such as emulsifiers, wetting agents, buffers, and the like.

In one embodiment of the invention a method for treating rheumatoid joints using the rAAV virions of the invention is provided. The method preferably comprises the steps of (a) establishing diagnosis of rheumatoid arthritis of a joint; (b) transducing rheumatoid synovial cells of the joint using a therapeutically effective amount of a pharmaceutical composition comprising a pharmaceutically acceptable excipient and rAAV virions, wherein the rAAV virions comprise a rAAVX vector comprising a nucleotide sequence encoding at least one therapeutic protein (or peptide) and, (c) optionally repeating step (b) after a certain period of time.

In the treatment method, the transduction of the synovial cells may be either in vivo or ex vivo. In case of ex vivo transduction the transduced and (re)administered cells may be either autologous or non-autologous.

In an alternative treatment, the method comprising transducing rheumatoid synovial cells ex vivo using a rAAV virion as defined above, optionally selecting the transduced cells, administering the transduced cells to a rheumatoid joint of a subject, and optionally repeating the administration after a certain period of time.

In a further aspect, the invention relates to the use of a virion as defined above for the manufacture of a medicament for the treatment of a rheumatoid joint. Preferably, the treatment comprises transducing rheumatoid synovial cells of the joint in vivo using a therapeutically effective amount of a pharmaceutical composition comprising a pharmaceutically acceptable excipient and the rAAV virion as defined above, and, optionally repeating the transduction after a certain period of time. Alternatively, the treatment comprises transducing rheumatoid synovial cells ex vivo using the rAAV virion, optionally selecting the transduced cells, administering the transduced cells to a rheumatoid joint of a subject, and optionally repeating the administration after a certain period of time.

The "synovium" or "synovial tissue" or "synovial cells" as used herein refers to the cellular lining covering the non-cartilaginous surfaces of the synovial joints, as further described in Tak (2000, Examination of the synovium and synovial fluid. In: Firestein G S, Panyani G S, Wollheim F A editors. Rheumatoid Arthritis. New York: Oxford Univ. Press, Inc. 55-68) and incorporated herein by reference. The synovium consists of the intimal lining layer (or synovial lining layer) and the synovial sublining (subsynovium), which merges with the joint capsule. The intimal lining layer comprises intimal macrophages (or macrophage-like synoviocytes or type A synoviocytes) and fibroblast-like synoviocytes (or type B synoviocytes). The term "rheumatoid synovium" or "rheumatoid synovial cells" or "rheumatoid synovial tissue" refers to the inflamed synovium of the joints of a subject suffering from rheumatoid arthritis. The rheumatoid synovium is characterized by intimal lining hyperplasia and by accumulation of T-cells, plasma cells, macrophages, B-cells, natural killer cells and dendritic cells in the synovial sublining. These accumulated cells are comprised in the definition of rheumatoid synovial cells.

In another embodiment of the invention relates to a rAAV virion comprising capsid proteins of AAV serotype 5 or AAV serotype 2, whereby the rAAV virion comprises a rAAVX vector, wherein the rAAVX vector comprises an expression element operably linked to a nucleic acid sequence encoding a therapeutic protein effective against rheumatoid arthritis. More preferably, the rAAV virion is a rAAV5 virion, comprising AAV5 capsid proteins, and wherein the rAAVX vector is a rAAV5 or rAAV2 vector, of which a rAAV2 vector is most preferred. The nucleic acid sequence encoding a therapeutic protein effective against rheumatoid arthritis is preferably as described above and the vector may further comprises a suicide gene as described above.

In another embodiment of the invention a rAAV5 virion comprising a rAAVX vector is provided, wherein the rAAVX vector comprises an expression regulatory element operably linked to a nucleic acid sequence encoding a therapeutic protein effective against rheumatoid arthritis, and wherein the rAAV5 virion has a transduction efficacy for synovial cells which is higher than that of rAAV2 virions. The transduction efficacy is preferably at least about twice as high, more preferably at least about 2.5 times as high, or even about 3 times as high. Transduction efficiency can be tested in vivo or in vitro (cultured synovial cells), by transducing the cells and assessing transduction using standard methods. Transduction efficacy can be assessed for example as shown in the Examples. Preferably a detectable reporter or marker gene is present in the rAAV vectors when assessing transduction efficacy.

Also envisaged are kits comprising one or more of the components required for carrying out the methods of the invention, such as for example a kit comprising one or more rAAVX vectors, rAAV virions, protocols, reagents, and the like.

Unless stated otherwise, the practice of the invention will employ standard conventional methods of molecular biology, virology, microbiology or biochemistry. Such techniques are described in Sambrook and Russell (2001) *Molecular Cloning: A Laboratory Manual*, Third Edition, Cold Spring Harbor Laboratory Press, NY, in Volumes 1 and 2 of Ausubel et al. (1994) *Current Protocols in Molecular Biology, Current Protocols*, USA and in Volumes I and II of Brown (1998) *Molecular Biology LabFax*, Second Edition, Academic Press (UK), *Oligonucleotide Synthesis* (N. Gait editor), *Nucleic Acid Hybridization* (Hames and Higgins, eds.), *CRC Handbook of Parvoviruses vol I and II* (P. Tijessen edt.), *Fundamental Virology* $2^{nd}$ *Edition, vol. I and II* (Fields and Knipe eds.), all incorporated herein by reference.

The following non-limiting Examples describe the identification of the methods and vectors of the invention.

EXAMPLES

Example 1

Figure 2:
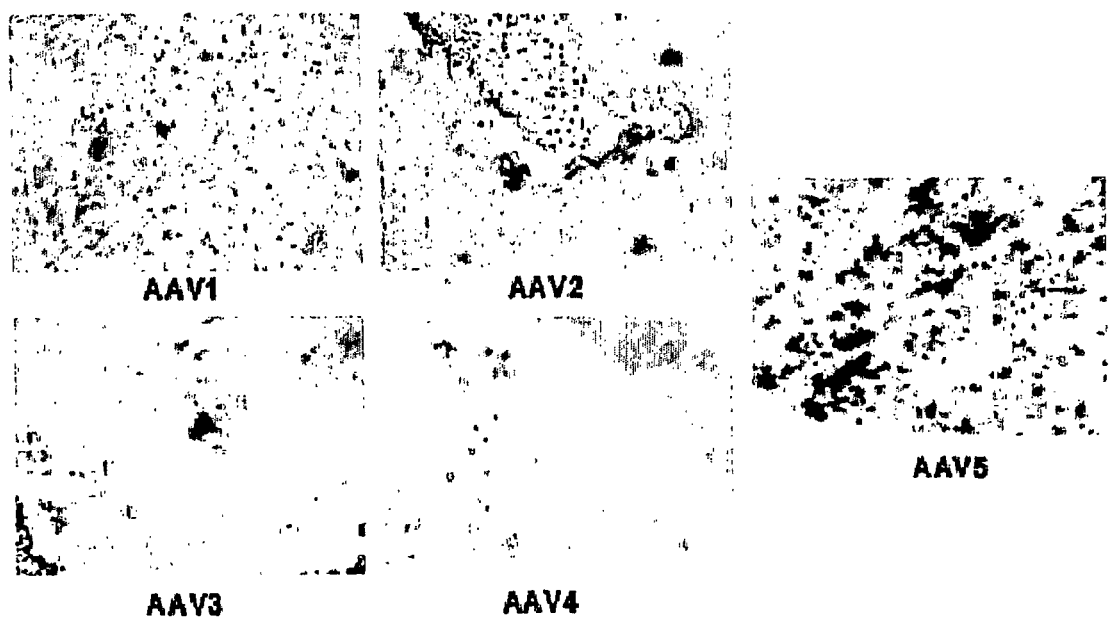
FIG. 2 Direct in-situ staining of χ-gal (blue) of frozen sections of rat joints injected with rAAV1 to rAAV5.
Figure 3:
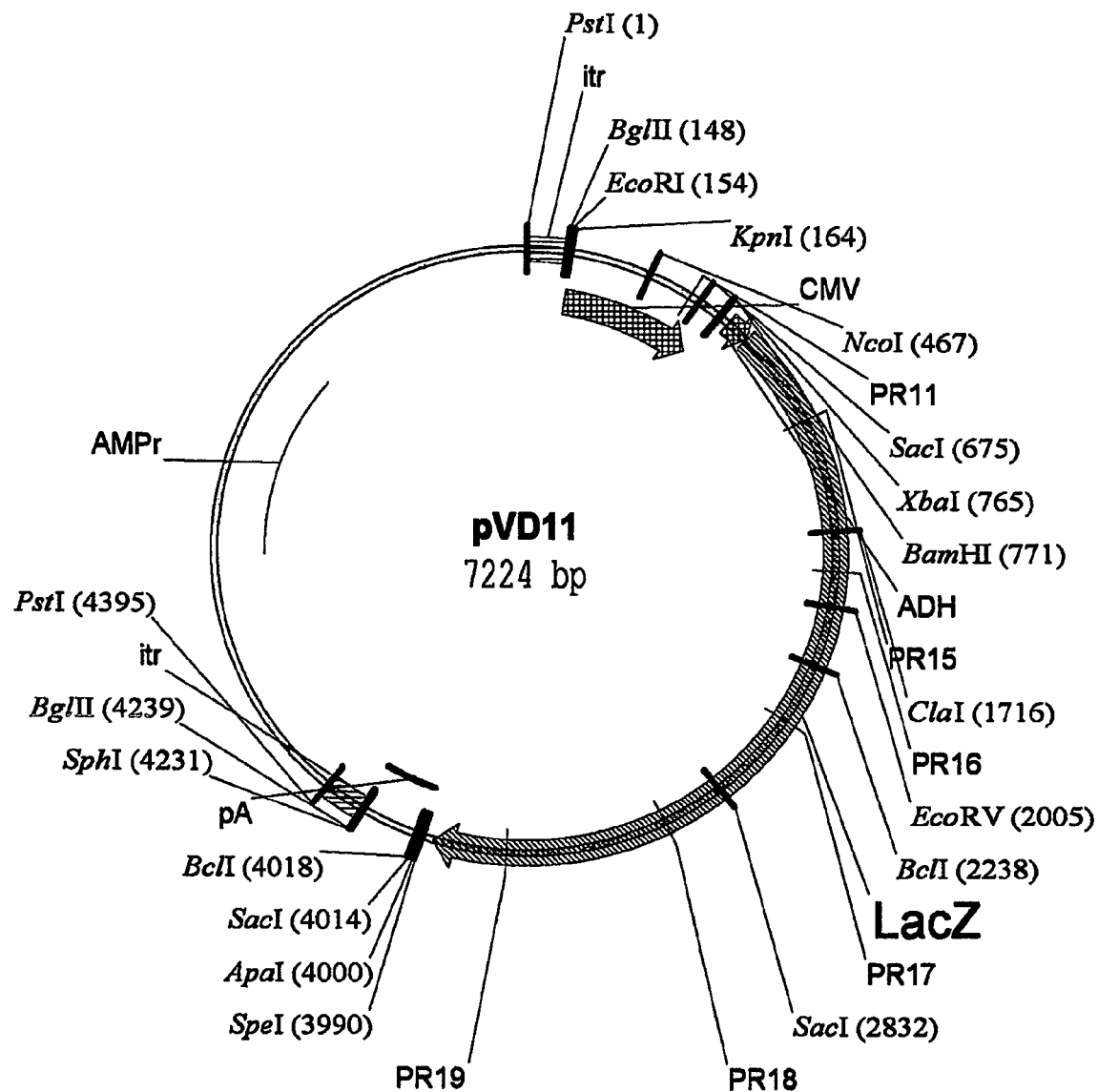
FIG. 3 Physical map of plasmid pVD11 containing an rAAV2 vector in which an expression cassette containing the *E. coli* lacZ coding sequences driven by the CMV promoter are flanked by AAV2 ITR sequences.

Production of Recombinant AAV Virions rAAV1 to rAAV5 virions were produced essentially as described by Grimm et al. (2002; Methods 28: 146-157), with particular reference to the method as summarized in Table 2 and FIG. 2 of this paper (we note that reference 21 in Grimm et al., 2002, supra, has now been published as Grimm et al., 2003, Mol. Therapy 7: 839-850). For the production of the rAAV virions the so-called two-plasmid method described in these Grimm et al. papers was used. Helper and expression plasmids were basically as described in these two papers by Grimm et al. (2002, 2003, supra), whereby the helper plasmid contains the viral backbone including the capsid proteins that determine the serotype of the virion. A particular expression plasmid used in the present invention is pVD11, in which a lacZ expression cassette is flanked by AAV2 ITR's.

pVD11 was constructed starting from pTRUF-2, which is described by Zolotukhin et al. (1996, J. Virol. 70: 4646-4654) and into which the Woodchuck hepatitis virus post-transcriptional regulation element (WPRE) was inserted to enhance the expression of the reporter gene (Xu et al., 2003, Biochim Biophys Acta. 11; 1621:266-71) and in which the GFP reporter gene was replaced by the E. coli lacZ gene as reporter gene.

As an example, the production of AAV5 virions containing pVD11 was as follows: 293 cells grown in roller bottles were transfected with pDP5 AAV helper plasmid and plasmid pVD11 using the calcium phosphate method (see e.g. Sambrook and Russell, 2001, supra, for calcium phosphate transfection). Cells were harvested after 3 days. Cells were lysed and virions were purified from the cell lysate using iodixanol gradients as described by Zolotukhin et al. (1999, Gene Ther. 6: 973-85). Iodixanol was subsequently removed and virions were further concentrated using diafiltration. The same procedure was used for the production of AAV-1, -2, -3, and -4 virions using the approriate serotype-determining helper plasmids as described in Grimm et al. (2002, supra).

Example 2

In Vivo Gene Delivery to Rats and Mice

A. Rats rAAV1 to rAAV5 virions, containing pVD11 vector (or other rAAV1 to rAAV5 vectors, not shown) comprising the gene coding for beta-galactosidase were injected into the right ankle joints of rats with adjuvant arthritis (AA) on day 12 after adjuvant immunization. Joints were harvested after 2 weeks and analyzed for beta-galactosidase expression by direct in-situ staining of frozen sections (FIG. 2), quantified by digital image analysis (FIG. 1), and RT-PCR.

Two weeks after injection of AAV-beta-Gal vectors the number of cells expressing beta-galactosidase in synovial tissue was assessed. In arthritic joints injected with rAAV5 virions a high number of cells expressed beta-galactosidase (111,441 IOD/mm$^2$), while in arthritic joints injected with rAAV2 virions only 38,212 IOD/mm$^2$ cells were counted (FIG. 1). No expression above background staining was observed for vectors derived from serotypes AAV1, AAV3 and AAV4. Expression of the transgene was confirmed by analyzing the joints by semi-quantitative PCR (data not shown).

B. Mice

In mice collagen-induced arthritis (CIA) rAAV virions comprising rAAV 1, rAAV2 and rAAV5 vectors containing the mSEAP gene were locally injected into the left knee joint 32 days following arthritis induction. Transgene expression was analyzed by RT-PCR in various organs for biodistribution, and by Elisa in sera and culture medium conditioned by the joint tissues at different time points.

In the CIA mice rAAV5 virions also provided a very high transduction efficiency. Transgene expression was detectable in sera and patellae one week after joint injection, increased overtime and plateaued for at least one month (5.31±1.59 and 1.94±1.97 ng/ml, respectively). No detectable expression was found for vectors based on serotypes AAV1 and AAV2.

Conclusions

Surprisingly it was found that transduction efficacy of vectors based on of different AAV serotype virions in experimental models of rheumatoid arthritis varied considerably, ranging from being completely ineffective to having a very high transduction efficiency (for vectors contained in AAV5 virions). The Examples clearly demonstrate that in vivo gene transfer with AAV5 virions was far more efficient than with the other serotypes and that rAAV5 virion is particularly suited for in vivo gene therapy of rheumatoid arthritis.

Example 3

Collagen-Induced Arthritis in Mice

Materials and Methods:
Recombinant AAV-2/2 and AA V-2/5 vectors.

Production of pseudotyped rAAVs (type 2 ITR based recombinant AAV genome packaged in AAV1, AAV2 or AAV5 capsid) was achieved by transient transfection as described by Allen, J. M et al. (Mol Ther, 2000, 1, 88). with the following modifications. Human embryonic kidney 293 cells were transfected with the adenovirus helper plasmid pXX6, the pAAV2 vector plasmid pGG2-CMV-muSEAP, which encode for a secreted form of the murine alkaline phosphatase under the transcriptional control of IE CMV promoter and the appropriate AAV packaging plasmid, which express the rep and cap genes. The packaging plasmids is pACG2.1 for rAAV2 and pLT-RC02 for rAAV-1/2 where the AAV2 rep gene is fused with AAV1 cap gene (a kind gift of R. Mulligan). The packaging plasmid was split in two for the production of rAAV-2/5 (pMTRep2 encoding AAV2 Rep proteins, a kind gift of D. Miller and pAAV5svori expressing AAV5 Rep and Cap proteins, a kind gift of J. Chiorini, requiring a quadruple transfection step. Recombinant vectors were purified by double CsCl2 ultracentrifugation gradient followed by extensive dialysis against sterile PBS. Physical particles were quantified by dot blot hybridization against a standard plasmid range. Titers are expressed as viral genome per ml (vg/ml). The rAAV-2/1-mSEAP, rAAV-2/2-mSEAP and rAAV-2/5-mSEAP titers were respectively 1.6×1012, 2.9×1012 and 2.7×1011 vg/ml. The rAAV-2/2 and -2/5 plasmids espressing the β-Gal transgene under the CMV promoter were flanked by the AAV-2 ITRs and encapsidates respectively in an AAV-2 or AAV-5 shell. Viral particles were produced by double transfection on 293 cells as previously described by Grimm, D. (Hum Gene Ther, 1998, 9, 2745), purified respectively using an iodixinol heparin column or a double CsCl gradient, and dialysed against PBS by the Vector Core of the University Hospital of Nantes. The rAAV titers were determined by dot blot and expressed as vector genome per ml (vg/ml). They were respectively 1.8×1011 and 3×1012 vg/ml for rAAV-2/2 and -2/5.

Animal Studies

Male DBA/1 mice (Harlan France) were bred in our facilities and used at the age of 8-10 weeks. Collagen-induced arthritis (CIA) was induced by intradermal injection at the base of the tail with 100 μl of collagen solution at 1 μg/μl at day 0. Bovine type II collagen (bCII) was diluted at 2 mg/ml (Sigma-Aldrich, St. Quentin Fallavier, France) with acetic acid 50 mM, and emulsified with an equal volume of Freund's complete adjuvant (Pierce, Bezons, France) before use. On day 21, animals were boosted with an intradermal injection of 100 μl bCII solution emulsified with an equal volume of Freund's incomplete adjuvant (Pierce, Bezons, France) before use. Following arthritis induction paw thickness was measured over time with a micrometer Mitutoyo (Sigma). On day 28, mice were synchronized with intra-peritoneal injection of 40 μg LPS (Sigma). When clinical signs for arthritis appeared, mice were anaesthetized by intra-peritoneal injection of a ketamine (30 mg/Kg) and xylazine (10 mg/Kg) solution. The skin above the knee was shaved, and indicated doses of AAV serotypes were injected intra-articularly in 5 μl of 0.9% NaCl into the left knee joint, by using a Hamilton syringe with a 30-gauge needle (NH-BIO, Massy, France). At day of sacrifice, whole knee joints were collected and froozen in liquid nitrogen for in situ quantification of β-gal staining on frozen sections. In experiments using the mSEAP reporter gene, blood samples were taken at various time before and after vector injection, and stored at −20° C. until tested. At day of sacrifice, left and right patellaes were collected and incubated 24 hrs in RPMI (200 μl). Supernatants were stored at −20° C. and patellaes were stored in liquid nitrogen until tested.

In Situ Staining for β-Galactosidase Transgene Expression.

Patellaes were placed in optimal cutting temperature (OCT) compround and immediately frozen in dry ice. Samples were cut on a cryostat and tissue sections fixed in 1.25% glutaraldehyde for 10 min, rinsed 3 times in PBS, placed overnight at 37° C. in X-Gal solution. Slides were then washed 3 times in PBS and counterstained with HE.

Serum muSeAP Quantification.

Blood samples were collected at the indicated time points following vector administration. Chemiluminescent detection allowed for enzyme activity quantification. Briefly, samples were centrifuged for 5 minutes at 2500 g to collect sera, endogenous alkaline phosphates was heat inactivated 5 min at 65° C. and the heat resistant muSeAP was measured by the addition of reaction buffer and CPSD chemiluminescent substrate according to the manufacturer's instructions (Tropix). Chemiluminescence was quantified on a luminometer (Mediators Diagnostika). Expression levels are expressed as ng of muSeAP per ml of serum according to a standard curve of purified human placental alkaline phosphatase.

Results

Intra-Articular Delivery of rAAV Serotypes in Mice Joints.

To compare the transduction efficiency of AAV serotypes in the joints, we delivered 50 particles of AAV-2/1, AAV-2/2 and AAV-2/5 expressing β-gal or mSEAP by direct injection into the joints of DBA/1 mice following onset of arthritis. Patellaes were harvested at 4 weeks for X-gal staining and immunohistochemistry, or for chemiluminescent detection of mSEAP in culture medium conditioned by the joint tissues.

Significant LacZ expression was detected in the joints of mice injected with both AAV-2/2- and AAV-2/5-LacZ, 4 weeks following vectors injection, with a significantly higher transduction efficiency observed with AAV-2/5. No staining could be observed in patellaes frozen sections from knees injected with AAV-1/5 or in the contra-lateral uninjected knee. The pattern of expression was similar to that previously reported, although a mild staining was observed in the synovial lining tissue, intense staining was revealed in the suprapatellar pouch. The staining was quantified by digital image analysis and showed that the transduction efficiency of AAV-2/5-LacZ was 3 times higher than AAV-2/2-LacZ. When using a secreted reporter gene such as the mSEAP, local transgene expression was 2 times higher with AAV-2/5 than with AAV-2/1 or AAV-2/2 and increased in the arthritic joints, compared with nonarthritic mice. Thus, AAV capside from serotype 5 appears more efficient to transduce intra-articular tissues than serotypes 1 or 2.

Dose Response of AAV-2/5

We next delivered increasing doses of AAV-2/2 or AAV-2/5 expressing β-gal or mSEAP (5×108, 1.5×109 and 5×109 particles) to determine if the better efficiency observed with AAV-2/5 was still true using higher doses into arthritic joints. Four weeks following gene delivery patellaes were harvested for X-gal staining and immunohistochemistry, or chemiluminescent detection of mSEAP in culture medium conditioned by the joint tissues and in sera. Increasing doses of AAV-2/5 resulted in increased levels of LacZ expression in the joint of mice. When using mSEAP as reporter gene, local transgene secretion was 2.6 times higher with 3 times more particles injected, while it was not modified with other capsids tested. Not surprisingly, the secreted transgene could also be detected in sera and the same range of increase in levels of expression was observed using increasing doses of virus. The highest dose of AAV-2/5-mSEAP vector tested was limited by the titer of the viral preparation and the maximal volume that could be injceted in mice joint (5 μl). It is likely that higher doses of AAV-2/5 (>5×109 particles) may result in even greater levels of transgene expression by arthritic joints.

Kinetic of Expression for AAV-2/5

We then investigated if the highest efficiency of AAV-2/5 compared with AAV-2/2 for transduction was due to slower transgene expression. Thus, we injected 1.5×109 particles of AAV-2/1, AAV-2/2 and AAV-2/5 expressing a secreted reporter gene mSEAP into the joints of arthritic DBA/1 mice and collected blood samples at the indicated time points. In AAV-2/5-mSEAP injected animals, transgene expression gradually increased from 7 days after administration to reach a maximum level at 3 weeks. On the contrary, AAV-2/1- and AAV-2/2-mSEAP were weakly detected at 3 and 4 weeks respectively. In a second experiment we showed that transgene expression remained stable for at least 19 weeks using AAV-2/5-mSEAP, while AAV-2/1-mSEAP gave a transitory expression of the transgene over 6 weeks, and AAV-2/2-mSEAP showed no detectable systemic transgene expression.

Example 4

Adjuvans-Induced Arthritis in Rats

Materials and Methods

Construction of Recombinant AAV

All rAAV contructs were derived from AAV2 and driven by the cytomegalovirus (CMV) promoter. Recombinant AAV was produced by co-transfection of 293 HEK cells with a packaging plasmid (pDG for AAV2 and pDP1, pDP3, pDP4 and pDP5 for AAV1, AAV3, AAV4 and AAV5 respectively) and a vector plasmid (pVD11) by the calcium phosphate method. The packaging plasmids contained all trans-acting elements: Cap-genes, Rep-genes, and adenoviral helper genes. The vector plasmid contained all cis-acting elements: ITRs, transgene, and CMV promoter.

Cells were seeded at a density of $3\times10^4$ cells/cm$^2$ four days prior to transfection in 850 cm$^2$ rollerbottles and were grown in 50 ml Dulbecco's Modified Eagle's Medium (DMEM) with glutamax-I (Invitrogen), 10% (v/v) Fetal Bovine Serum (FBS) (JRH), 60 U/ml Pencillin/Streptomycin (PS) (Invitrogen) at 37° C. Before transfection, medium was replaced with Iscove's Modified Dulbecco's Medium (IMDM; Invitrogen) and at 16 h post transfection the medium was replaced with 50 ml of fresh DMEM/FBS/PS. At 72 h post transfection, the cells were harvested in 10 ml 50 mM Tris.HCl pH 8.5, 150 mM NaCl, 1 mM MgCl$_2$, 0.1% (v/v) Triton X-100. Finally, benzonase (Merck) was added to the lysate to a final concentration of 75 U/ml.

Crude cell lysates were further purified with iodixanol gradients. Iodixanol step gradients were made in Beckman Quick-seal tubes (25×89 mm, Beckman). Step gradients were loaded by placing a pasteurs pipet into the tube. From top to bottom: 15 ml crude cell lysate, 9 ml 15% iodixanol+1M NaCl in PBS-MK (PBS+1 mM MgCl$_2$+2.5 mM KCl), 6 ml 25% iodixanol in PBS-MK, 5 ml 40% iodixanol in PBS-MK, 5 ml 60% pure iodixanol. Thereafter, the tube was sealed and centrifuge for 1 hour at 69.000 rpm 16° C. After centrifugation the 40% iodixanol step from the gradients was extracted. The 40% iodixanol containing virus solution was diluted 10 times with PBS-MK and concentrated to approximately 2 ml with centricon devices (YM-100, Millipore). Stock titers ranging between $10^{11}$-$10^{12}$ genomic copies (GC)/ml were reached.

Local Gene Transfer

Pathogen-free male Lewis rats (150-200 g) were obtained from Harlan Sprague Dawley Inc. (Horst, The Netherlands) and were maintained in our central animal facility. All rats were immunized at the base of the tail with 1 mg of *Mycobacterium tuberculosis* H37RA (Difco, Detriot, Mich.) in 0.1 ml mineral oil on day 0. Paw swelling was usually observed by day 10-12 and measured daily by water displacement plethysmometry. The right ankle joints were injected at day 12 after immunization in animals anesthetized with isoflurane. The skin was prepared with ethanol and rAAV1 to 5 containing the gene for LacZ (further revered to as rAAV1 to 5) were injected anterolaterally into the right ankle joint in a total volume of 50 µl saline using 31-gauge needle on a glass syringe. The animals were injected with $6.1\times10^{10}$ GC's (n=6/group). Adenovirus containing LacZ (adjusted to $6.1\times10^{10}$ GC/animal) served as a positive control, whereas saline was used as negative control. AAV and saline injected rats were sacrificed two weeks after intra-articular injection by CO$_2$ inhalation, adenovirus injected rats were sacrificed two days after injection. Serum samples were taken by bleeding the vena cava.

To investigate the transgene expression at different time points, a second experiment was performed using a different batch of rAAV. Animals received an i.a. injection of $1.14\times10^{10}$ GC's rAAV2 or rAAV5 and were sacrificed as described one, two, three and four weeks after injection (n=3). Serum samples were obtained from all groups by tail bleeding before AAV injection and by vena cava punction during sacrificing.

Detection of Transgene Products

In Situ Staining of Beta gal

Joints were decalcified using EDTA and snap frozen in liquid nitrogen. Ten µm sections were cut and mounted on glass slides. Detection of β-galactosidase (β-gal) was performed by X-gal staining. Briefly, tissue was fixed in 0.25% glutaraldehyde/4% paraformaldehyde for 10 min at 4° C. Thereafter, samples were washed twice with PBS and stained in staining solution containing 1 mg/ml X-gal (5-bromo-4-chloro-3-indolyl-β-D-galactoside), 2 mM MgCl2, 5 mM K$_3$Fe(CN)$_6$, 5 mM K$_4$Fe(CN)$_6$, and 0.1% triton x-100 in PBS overnight at 37° C. After washing with PBS, sections were counterstained with nuclear red. The sections were analyzed by digital image analysis for β-gal positive cells.

Digital Image Analysis

Five randomly selected fields within each section were chosen for digitizing the amount of positive signal. These images were acquired on an Olympus microscope (Olympus, Tokyo, Japan), captured using a Charged Coupled Device video camera (Sony, Tokyo, Japan) and digitized with a PV100 multimedia 16 bit color video digitizer card. In the resultant color images the area of positive staining and the mean optical density (MOD) were measured by a macro program. The MOD is proportional to the cellular concentration of protein. The integrated optical density (IOD) is equal to the MOD multiplied by the area of positive staining.

Real Time-PCR detection of LacZ

Ankle joints (trimmed of skin) and organs were snap frozen in liquid nitrogen, pulverized using a mortar, and homogenized in 1 ml of TRIzol Reagent (GibcoBRL Life Technologies) using a tissue homogenizer. Total RNA was isolated from the aqueous phase and genomic DNA (gDNA) was extracted from the phenol-chloroform phase according to the manufacturer's instructions. gDNA was stored for Q-PCR analysis. RNA was dissolved in DEPC-water and quantified by spectrophotometry. cDNA was synthesized using 1 µg RNA and 0.5 µg Oligo(dT) (GibcoBRL), 5× First-Strand-buffer, 0.1 M DTT, dNTP Mix (10 mM each), and 1 µl of Superscript II RT (Invitrogen). For RT-PCR, 10 µl of cDNA solution was amplified using 25 µl of Accuprime SuperMix I (Invitrogen Life technologies), 215 mM of the LacZ1 primer (forward, 5'-GCA-TCG-AGC-TGG-GTA-ATA-AGC-GTT-GGC-AAT-3') (SEQ ID No. 1) and 215 mM of the LacZ2 primer (reverse, 5'-GAC-ACC-AGA-CCA-ACT-GGT-AAT-GGT-AGC-GAC-3') (SEQ ID No. 2) in a total volume of 50 µl. Amplification was then performed in a thermocycler (MJ Research, Inc.) as follows: 3 min at 95° C. followed by 35 cycles of 94° C. for 1 min, 58° C. for 90 sec and 72° C. for 1 min, respectively, followed by a final extension phase at 72° C. for 10 minutes. The PCR products were analyzed by standard agarose gel electrophoresis on a 0.9% agarose gel containing ethidium bromide for UV-assisted visualization of the 622 bp product.

Detection of Viral Genomic Copies by Quantitative-PCR

To determine the viral titer in temis of genomic copies (full viral particles), AAV samples were first diluted 10-fold in PBS. Subsequently, 5 µl of these dilutions were added in duplicate to 45 µl of 0.25 mg/ml DNAseI, PBS. The mixtures were incubated for 20 min at 37° C., after which 75 µl 2.75 mg/ml proteinase K, 8.6 mM Tris.HCl pH 8.0, 86 mM NaCl, 8.6 mM EDTA, 0.43% (w/v) SDS was added. After incubation for 60 min at 37° C., 115 µl 14 µg/ml polyA, SV RNA lysis buffer (Promega) was added per well. Samples were incubated with 10 µl of MagneSil BLUE suspension (Promega) and viral DNA was isolated using the MagnaBot 96 Magnetic Separation Device (Promega) according to the supplier's instructions. Dilutions of the purified viral DNA or the gDNA isolated from the joints and organs were added to PCR mix (0.5 µM CMV forward primer (5'AATGGGCGG-TAGGCGTGTA3') (SEQ ID No. 3) (Invitrogen), 0.5 µM CMV reverse primer (5'AGGCGATCTGACGGTTCAC-TAA3') (SEQ ID No. 4), (Invitrogen), and SYBR green PCR master mix buffer (Applied Biosystems). DNA standards used were 10-fold serial dilutions of 10 E+1 to 10E+8 copies of pVD23. PCR reactions were performed using the Abi prism SDS7000 sequence detection system (Applied biosystems).

Determination of Neutralizing Antibodies Against rAAV in Serum

Neutralizing antibody titers were analyzed by assessing the ability of serum antibody to inhibit the transduction of AAV into COS cells. Various dilutions of serum (1:200 to 1:5200) were pre-incubated with rAAV at 37° C. for 1 hour and then added to 80% confluent cells. Thereafter, cell cultures were incubated with AAV in the presence of serum for 20 hours and LacZ expression was measured by X-gal staining. The antibody titer was represented by the highest dilution which gave no inhibition of β-gal expression compared to cells incubated with AAV alone.

Cell Culture of Human FLS

Small-bore arthroscopy (2.7 mm arthroscope, Storz, Tuttlingen, Germany) was performed under local anesthesia in patients with established RA.

The obtained biopties were enzymatically dispersed. Briefly, synovium was minced and incubated with 1 mg/ml collagenase type VIII (Sigma) in serum free DMEM (Gibco) for 3 h at 37° C. Thereafter, cells were extensively washed and cultured in DMEM/10% fetal calf serum (FCS) in a humidified 5% $CO_2$ atmosphere. Cells were allowed to adhere overnight and nonadherent cells were removed. Adherent FLS were grown in DMEM/10% FCS and split 1:3 at 80-90% confluence. The human FLS were used from passage 3 to 10.

In Vitro Gene Transduction in FLS

FLS were plated on 96-wells dishes (Falcon) at $8 \times 10^3$/well. After incubation for 10 hours, $8 \times 10^7$ GCs of rAAV2 and rAAV5 containing the genes for LacZ or green fluorescent protein (GFP) were added to each well in medium containing 10%. The cells were cultured for 48 hours and marker gene expression was evaluated by enzymatic staining or fluorescent microscopy. Three independent FLS cell lines were used for these experiments.

Results

Comparative Efficiency of Five AAV Serotypes

To compare the transduction efficiency of AAV serotypes in the joints, rAAV1 to rAAV5 were injected in the right ankle joints of rats on day 12 after adjuvant immunization. Joints were harvested two weeks after injection and stained in situ for β-gal expression. Transgene expression was quantified by digital image analysis. The most abundant β-Gal expression was observed in arthritic joints injected with rAAV5. Strikingly, AAV transduction resulted in a greater penetration into the synovial tissue compared to adenovirus, showing β-gal expression just in the lining. In the contralateral uninjected and control joints no staining could be observed. Using digital image analysis the highest number of cells expressing β-Gal in synovial tissue was detected in arthritic joints injected with AAV5, followed by a much lower expression using AAV2 (111441 and 38212 IOD/mm2, respectively). No expression above background staining was observed for serotype 1, 3 and 4.

Duration of Transgene Expression

Figure 4:
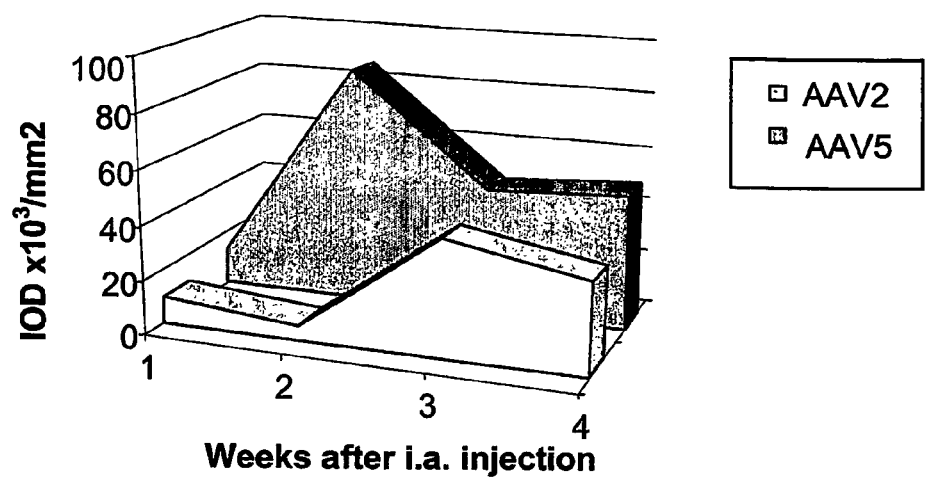
FIG. 4: Beta-gal expression in rat synovial tissue 1, 2, 3 and 4 weeks after i.a injection of rAAV 2 and 5, quantified by digital image analysis.

To study the transgene expression over time, rAAV2 and rAAV5 were injected in arthritic joints of rats and sacrificed one, two, three and four weeks after injection of the vector. Both serotypes demonstrated a significant expression for up to four weeks, which was already present one week after injection. However, rAAV5 showed earlier and at all time points a higher β-gal expression as quantified by digital image analysis (FIG. 4). Injected joints were snap frozen and cryosections were stained in situ for beta-gal activity. The amount of blue staining per section was analyzed by digital image analysis and expressed as cumulated $IOD/mm^2$ (IOD: Integrated Optical Density).

This was confirmed by Q-PCR analysis. A higher amount of genomic copies was detected at all time points after rAAV5 injection compared to the rAAV2 injected joints Table 1:

TABLE 1

Detection of viral genomic copies in injected joints after i.a. injection of AAV2 or AAV5. Genomic DNA was isolated from crushed ankle joints 1, 2, 3 and 4 weeks after AAV injection. qPCR was performed with specific primers for the CMV promoter. Values expressed as GC/μg gDNA ± stdev.

|  | AAV2 | | AAV5 | |
| --- | --- | --- | --- | --- |
| Week 1 | 6.45E+04 | ±2.12E+03 | 1.42E+07 | ±3.39E+03 |
| Week 2 | 1.83E+03 | ±5.87E+02 | 1.37E+06 | ±5.17E+03 |
| Week 3 | <10 copies | | 4.37E+06 | ±2.25E+03 |
| Week 4 | <10 copies | | 2.24E+05 | ±1.49E+03 |

In order to detect LacZ transcription in the joints RT-PCR analysis was carried out using specific primers. We found transcription of the transgene in joints injected with rAAV5 at all time points showing minimal differences in intensity, whereas the amount of LacZ mRNA was below the detection limit of our assay in the rAAV2 injected joints.

Formation of rAAV Antibodies

Figure 5:
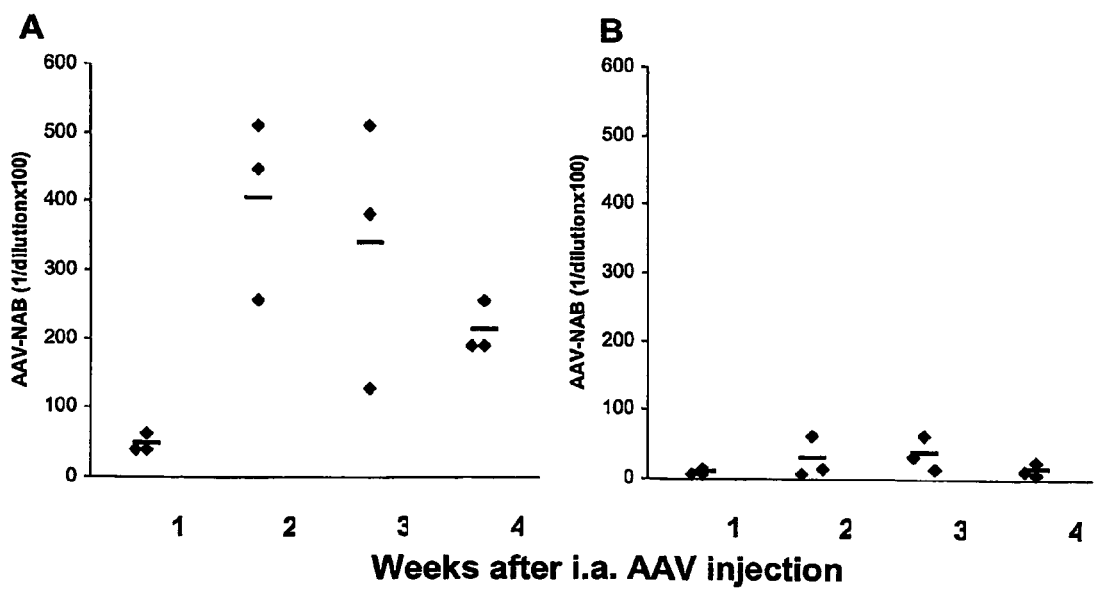
FIG. 5: Development of neutralizing antibodies in serum after intraarticular injection of rAAV2 or rAAV5.

To detect a possible humoral immune response against the rAAV capsid proteins, after local intra-articular injection we performed a specific assay as described in the Methods section. The presence of neutralizing antibodies before and after rAAV injection was determined in the serum of rats injected with rAAV2 and 5. Results are shown in FIG. 5. Arthritic rats were injected with $1.14 \times 10^{10}$ GC's rAAV2 (A) or rAAV5 (B) into the right ankle joints. Serum samples were obtained 1, 2, 3 and 4 weeks after injection. Titers were calculated as the highest dilution which shows no inhibition of X-gal positive cells compared to wells incubated with rAAVLacZ alone.

Before injection, no antibodies were found in any of the samples. One week after injection, neutralizing antibodies were detected, peaking at 2 weeks and slowly decreasing after 3 weeks. Although this trend is seen for both serotypes, rAAV2 injection clearly induces higher neutralizing antibodies titers in the serum then rAAV5, showing only levels slightly above background. Importantly, no cross-reactivity was found for the two serotypes.

Example 5

Transduction of Human FLS with rAAV2 and rAAV5

Having shown that rAAV2 and 5 are able to transfect rat synovium, we wanted to investigate the potential of both serotypes to transduce primary human FLS obtained from patients with RA. For this purpose we used rAAV vectors either expressing LacZ or GFP. Transgene expression was visualized after 48 hours by enzymatic β-gal staining or fluorescent microscopy. Both serotypes were capable of transducing human FLS, with rAAV5 showing a higher expression in all experiments. In FIG. 6 a representative experiment is shown.

The invention claimed is:

1. A method for increasing expression of a therapeutic protein in a joint of a subject with rheumatoid arthritis (RA) consisting of the step of delivering a recombinant AAV5 (rAAV5) virion to a rheumatoid synovial cell in a joint of a subject with RA by injection into the joint, which virion consists essentially of the following components:
   (a) a capsid protein of AAV serotype 5 (AAV5), and
   (b) a recombinant adeno-associated virus type 2 (rAAV2) vector comprising a nucleotide sequence encoding a therapeutic protein to which is operably linked a promoter and expression elements;
   wherein an injection of said rAAV5 virion into said joint results in transduction of the synovial cell and an increase in expression of said therapeutic protein in said subject compared to expression following an injection of an equivalent dose of a virion that comprises (i) said rAAV2 vector of (b) and (ii) an AAV2 capsid protein in a second subject with RA.

2. The method according to claim 1, wherein the therapeutic protein is selected from the group consisting of: IL-1 inhibitor, TNFα inhibitor, IL-1 receptor antagonist, IL-18 binding protein, sTNFα receptor p55, sTNFα p75, dn-IKK-β, IL-4, IL-10, IL-13, IFN-β and vasoactive intestinal peptide (VIP).

3. The method according to claim 2, wherein the therapeutic protein is IFN-β.

4. The method according to claim 1 wherein said therapeutic protein is expressed in said subject for at least six weeks.

5. The method according to claim 4 wherein said therapeutic protein is expressed in said subject for at least 19 weeks.

6. The method according to claim 1 wherein said rAAV5 virion is in a pharmaceutically acceptable excipient.

7. The method according to claim 6 wherein the delivering step is repeated.

8. The method according to claim 1 wherein said therapeutic protein is expressed in said subject for at least one month.

9. The method according to claim 1 wherein the subject is human.

10. The method according to claim 1 wherein a single injection of said rAAV5 virion into said joint results in transduction of the cell and an increase in expression of the therapeutic protein.

* * * * *